(12) United States Patent
Crisler

(10) Patent No.: US 11,590,187 B2
(45) Date of Patent: Feb. 28, 2023

(54) ANTIMICROBIAL COMPOSITIONS

(71) Applicant: Shaman Naturals, LLC, Rock Springs, WY (US)

(72) Inventor: Maria Crisler, Rock Springs, WY (US)

(73) Assignee: Shaman Naturals, LLC, Rock Springs, WY (US)

( * ) Notice: Subject to any disclaimer, the term of this patent is extended or adjusted under 35 U.S.C. 154(b) by 0 days.

(21) Appl. No.: 17/248,208

(22) Filed: Jan. 14, 2021

(65) Prior Publication Data

US 2022/0347245 A1  Nov. 3, 2022

Related U.S. Application Data

(60) Provisional application No. 62/960,932, filed on Jan. 14, 2020.

(51) Int. Cl.
*A61K 36/185* (2006.01)
*A61K 31/05* (2006.01)
*A61K 47/55* (2017.01)
*A61K 47/44* (2017.01)
*A61K 31/12* (2006.01)

(52) U.S. Cl.
CPC ............ *A61K 36/185* (2013.01); *A61K 31/05* (2013.01); *A61K 31/12* (2013.01); *A61K 47/44* (2013.01); *A61K 47/551* (2017.08)

(58) Field of Classification Search
None
See application file for complete search history.

(56) References Cited

U.S. PATENT DOCUMENTS 6,630,507 B1 * 10/2003 Hampson et al.

* cited by examiner

*Primary Examiner* — Michael V Meller
(74) *Attorney, Agent, or Firm* — Frost Brown Todd LLP

(57) ABSTRACT

Embodiments of the invention are directed to compositions containing cannabinoid, cannabidiol, cannabidiol isomer, or cannabidiol analog and combinations thereof for treating microbial infections, and methods for treating microbial infections by topically administering compositions containing cannabinoid, cannabidiol, or cannabidiol analog to the patient in need of treatment.

1 Claim, 3 Drawing Sheets

ANTIMICROBIAL COMPOSITIONS

A. CROSS-REFERENCE TO RELATED APPLICATIONS

This application claims priority from U.S. Provisional No. 62/960,932, entitled "Antimicrobial Compositions," filed on Jan. 14, 2020 the entirety of which is hereby incorporated by reference.

B. GOVERNMENT INTERESTS

Not applicable

C. PARTIES TO A JOINT RESEARCH AGREEMENT

Not applicable

D. INCORPORATION OF MATERIAL ON COMPACT DISC

Not applicable

E. BACKGROUND

Skin is constantly in contact with their surrounding environment, exposing skin to diseases caused by bacteria and fungi ("Microbes"). Numerous microbes are capable of infecting the skin causing inflammation, discoloration, itching, burning, and various other symptoms. For example, bacterial infections can be caused by staphylococci or streptococci. Toxins excreted by Staphylococcus bacteria during infection can cause, boils, impetigo, food poisoning, cellulitis, toxic shock syndrome, abscesses, and antibiotic resistant staphylococci, like MRSA, can cause necrosis and death. Streptococci can cause wound and skin infections as well as pharyngitis and pneumonia.

Other bacteria such as *Propionibacterium acnes* can cause acne. Acne (Acne vulgaris) is a common bacterial infection caused by *Propionibacterium acnes*. During an outbreak, *Propionibacterium acnes* bacteria infect sebaceous glands, causing inflammation and resulting in the formation of inflamed papulae, surface cysts, atheromatous cysts and pustules, and "blackheads." About 85% of the human population experiences acne often associated with maturation.

Fungal infections ("mycoses") include excessive growth of fungi that are normally present in or on the body of a subject or the growth of fungi that are not normally present in or on a subject. Fungi can infect or cause an allergic or inflammatory reaction in most any part of the body, both in immunocompetent and immunocompromised patients. There are 500 fungi known to infect humans, and a few of them are lethal. The most commonly reported fungal infections are *Candidiasis*, both *Candida albicans* and *C. non-albicans*, and *Aspergillus*.

Superficial mycoses are caused by fungi that grow on the outermost layer of the skin and hair and cause little or no inflammatory response. An example of superficial mycoses is *Tinea versicolor*. *Tinea versicolor*, which frequently occurs in teens and young adults, interferes with pigmentation, causing discolored patches of skin.

Cutaneous mycoses extend into the epidermis and include invasive hair and nail diseases. Examples of cutaneous mycoses include athlete's foot and ringworm. Common symptoms of these infections include itching, burning, redness, blisters, peeling, cracking, and scaling of the skin. Cutaneous mycoses also include mucocutaneous mycoses such as oral thrush, vaginal thrush, and penile thrush. Symptoms for oral thrush include white patches on the tongue or other areas of the mouth and throat and may also include soreness and problems with swallowing. Symptoms of vaginal thrush include genital itching, burning, and white discharge from the vagina. Penile thrush is less common, and causes itchiness. Other examples include onychomycosis, which is a fungal infection of the nail.

Subcutaneous mycoses penetrate into the dermis, subcutaneous tissues, muscle, and fascia after inoculation of the fungi into these tissues. These infections are difficult to treat and may require surgical removal. Examples of subcutaneous mycoses include chromoblastomycosis, mycetoma, and sporotrichosis. Chromoblastomycosis is characterized by verrucous lesions of the skin of the lower extremities, which start as small red or grey bumps and grow into warty dry nodules or plaques. New lesions may develop as satellites. Chromoblastomycosis is limited to subcutaneous tissue, with no involvement of bone, tendon, or muscle. In contrast, mycetoma involves the contiguous bone, tendon, and skeletal muscle and is characterized by the formation of grains containing aggregates of the fungi that may be discharged onto the skin surface through sinuses. Sporotrichosis is an infection of the skin caused by a fungus related to the mold of stale bread. The symptoms include firm but painless bumps on the skin that can range in color from pink to purple. The bumps may develop into an open sore that may drain clear fluid. Untreated sores may become chronic. The mold may spread along the lymph nodes and new nodules and sores spread in a line up the infected arm or leg.

F. SUMMARY OF THE INVENTION

Various embodiments are directed to antimicrobial compositions including cannabinoids, and methods for treating bacterial and fungal infections using such compositions.

G. DESCRIPTION OF THE DRAWINGS

Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention. In the following description, numerous specific details are set forth in order to provide a thorough understanding of the present invention. The present invention may be practiced without some or all of these specific details. In other instances, well known process operations have not been described in details so as to not unnecessarily obscure the present invention.

H. DETAILED DESCRIPTION

Figure 1A:
FIG. 1A is a photograph showing a patient exhibiting symptoms of the acne before treatment with the compositions of the invention.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 ml to 8 ml is stated, 2 ml, 3 ml, 4 ml, 5 ml, 6 ml, and 7 ml are also intended to be explicitly disclosed, as well as the range of values greater than or equal to 1 ml and the range of values less than or equal to 8 ml.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g, "about 50" means 45 to 55, "about 25,000" means 22,500 to 27,500, etc, unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g, more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

The term "disorder" is used in this disclosure to mean, and is used interchangeably with the terms disease, condition, symptom, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance the texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc, which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government, or listed in the U.S. Pharmacopeia or other generally recognized pharmacopeia for use in mammals (e.g, animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, aryl aliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

The term "herb" is used herein, for instance, in reference to plants that in certain embodiments and delivered by appropriate methods have a therapeutic or medicinal purpose, such as, but not limited to river mint, eucalyptus, wattle, cocoa, plants of the family cannabaceae, plants containing cannabinoids, and plants containing cannabinoid precursors and analogs.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments are directed to compositions for treating dermatological microbial infections containing cannabinoids and methods for using such compositions to treat, prevent, and ameliorate microbial infections. In certain embodiments, the composition may include one or more brassinosteroids. Particular embodiments are directed to methods for treating microbial infections by administering the compositions described above. Such compositions may be administered topically in therapeutically effective doses. The compositions and methods of the invention may reduce symptoms and proliferation of microbial infections.

As used herein, the term "microbe" or "microbial" shall encompass various bacteria and fungi that cause dermatological diseases.

The compositions of the invention have a general antimicrobial effect. Bacterial infections treated using compositions and methods of embodiments are not limited and include, for example, *Staphylococci, Streptococci, Propionibacterium, Cutibacterium, Corynebacterium*, and the like and combinations thereof. The fungi treated using the compositions and methods of embodiments are not limited. For example, fungal infections can be caused by *Aspergillus, Blastomyces, Candida, Coccidioides, Cryptococcus, Histoplasma, Pneumocystis, Coccidioides, Stachybotrys, Microsporum, Epidermophyton, Trichophyton*, and the like and combinations thereof. Compositions of embodiments may produce a reduction in symptoms associated with microbial infection, while improving the condition of the affected skin, mucosa, and other tissues following treatment.

The cannabinoids of such embodiments include any of a broad class of compounds that are known to interact with cannabinoid receptors, and encompass endocannabinoids (produced naturally in the body by animals), the phytocannabinoids (found in cannabis and some other plants), and synthetic cannabinoids (manufactured artificially). Example cannabinoids include, but are not limited to, tetrahydropyran analogs, such as, $\Delta^9$-tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol, (−)-(3S,4S)-7-hydroxy-delta-6-tetrahydrocannabinol-1,1-dimethylheptyl, (+)-(3S,4S)-7-hydroxy-$\Delta$-6-tetrahydrocannabinol, and $\Delta^8$-tetrahydrocannabinol-11-oic acid, piperidine analogs, such as, (−)-(6S,6aR,9R,10aR)-5,6,6a,7,8,9,10,10a-octahydro-6-methyl-1-3-[(R)-1-methyl-4-phenylbutoxy]-1,9 phenanthridinediol 1-acetate), aminoalkylindole analogs, such as, (R)-(+)-[2,3-dihydro-5-methyl-3-(4-morpholinylm-ethyl)-pyrrolo[1,2,3,-de]-1,4-benzoxazin-6-yl]-1-naphthelenyl-methanone, open pyran-ring analogs, such as, 2-[3-methyl-6-(1-methylethenyl-2-cyclohexen-1-yl]-5-pentyl-1,3-benzendi-ol, and 4-(1,1-dimethylheptyl)-2,3'-dihydroxy-6'-α-(3-hydroxypropyl)-1',−2',3',4',5',6'-hexahydrobiphenyl, lipophilic alkylamides, such as, dodeca-2E,4E,8Z,10E/Z-tetraenoic-acid-isobutyl-amide, cannabinoid mimetics, salts, solvates, metabolites, and metabolic precursors of these compounds and combinations thereof. In some embodiments, the cannabinoids may be derived plants including hemp, *Echinacea purpurea, Echinacea angustifolia, Acmella oleracea, Helichrysum umbraculigerum, Radula marginata*, and combinations thereof and oils made from these plants, and in other embodiments, the cannabinoids may be manufactured or chemically synthesized.

The compositions of various embodiments can include any number of cannabinoids in various concentrations; however, in certain embodiments, the cannabinoid may be cannabidiol (2-(6-isopropenyl-3-methyl-5-cyclohexen-1-yl)-5-pentyl-1,3-benzenediol, CBD) or cannabigerol (2-[(2E)-3,7-Dimethylocta-2,6-dienyl]-5-pentyl-benzene-1,3-diol, CBG). Cannabidiol and cannabigerol each have 7 double bonds and 30 stereoisomers. Embodiments include compositions containing each stereoisomer individually and compositions containing a combination of these stereoisomers.

In some embodiments, the cannabinoids in the composition may be cannabidiol analogs. The term "cannabidiol analogs" refers to synthetically produced compounds that are structurally similar, but not structurally identical, to cannabidiol. Various cannabidiol analogs are known in the art and embodiments encompass such cannabidiol analogs. For example, PCT Publication WO2017/132526 and U.S. Pat. No. 6,630,507, which are each hereby incorporated by reference in their entirety, describes various analogs of cannabidiol. In some embodiments, the analogs of cannabidiol may be of general Formula I:

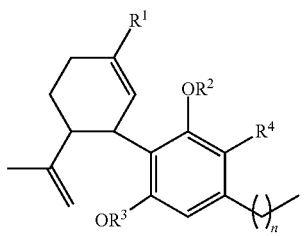

where $R^1$ is hydrogen, methyl, linear or branched $C_2$-$C_{10}$ alkyl, linear or branched $C_2$-$C_{10}$ alkenyl, linear or branched $C_2$-$C_{10}$ substituted alkyl, linear or branched $C_2$-$C_{10}$ substituted alkenyl, $R^2$ and $R^3$ are each, individually, hydrogen, methyl, linear or branched $C_2$-$C_{10}$ alkyl, linear or branched $C_2$-$C_{10}$ substituted alkyl, linear or branched $C_2$-$C_{10}$ alkenyl, linear or branched $C_2$-$C_{10}$ substituted alkenyl, linear or branched $C_2$-$C_{10}$ acyl, linear or branched $C_2$-$C_{10}$ substituted acyl, an amine or amino acid, amino acid ester, $R^4$ is hydrogen, substituted or unsubstituted alkyl, carboxyl, alkoxy, aryl, aryloxy, arylalkyl, halo or amino, and n may an integer of 2 to 10 and the like and salts and solvates thereof. In some embodiments, $R^2$ and $R^3$ may, independently, be a linear or branched, substituted or unsubstituted $C_2$-$C_{10}$ acyl having a carboxylic acid terminus thereby producing a dicarboxylic acid, and salts thereof. Like cannabidiol, cannabidiol analogs can have various isomers. Embodiments include all isomers of such cannabidiol analogs.

In some embodiments, cannabidiol analogs, such as those described above may be combined with cannabidiol, to produce a mixture of cannabidiol and cannabidiol analogs. Thus, as used herein the term "cannabidiol" encompasses cannabidiol, cannabidiol analogs, and the various isomers of cannabidiol and cannabidiol analogs.

In certain embodiments, the cannabidiol of embodiments described above may be cannabidiolic acid ("CBDA"). Without wishing to be bound by theory, CBDA may exhibit improved hydrophilicity over other isomers of cannabidiol, which may allow for improved solubility and delivery of CBDA to the skin. The CBDA may be modified, partially digested, or otherwise acted upon by enzymes in the skin to produce for example cannabidiol (CBD) or cannabigerol (CBG), which may be the active form cannabidiol in the composition. Thus, CBDA may act as a prodrug in some embodiments of the invention. Other cannabidiol analogs or isomers may produce a similar effect and are encompassed by prodrug embodiments of the invention.

The compositions of various embodiments can include up to about 50% (w/w) cannabidiol, cannabidiol analogs, isomers of cannabidiol, cannabidiol analogs, and combinations thereof (collectively, "cannabidiol"), and in some embodiments, the compositions may include from about 50% (w/w) to about 0.5% (w/w), about 30% (w/w) to about 1% (w/w), about 20% (w/w) to about 1% (w/w), about 20% (w/w) to about 5% (w/w) cannabidiol, or any range of or individual concentration encompassed by these example ranges. In particular embodiments, the composition may include about 15% (w/w) to about 10% (w/w) cannabidiol.

Cannabidiol can be obtained by cold-pressing industrial hemp with trace amounts of THC. Cannabidiol in this present invention is provided as a natural constituent of hemp oil. The cannabidiol in the compositions of embodiments of the invention may be 100% cannabidiol, or oils, solvents, and emulsions containing cannabidiol. For example, in some embodiments, the compositions of the invention may include cannabidiol derived from hempseed oil. Hempseed oil is generally manufactured from varieties of *Cannabis sativa* that do not contain significant amounts of tetrahydrocannabinol (THC), the psychoactive element present in the cannabis plant. This manufacturing process typically includes cleaning the seed to 99.99% before pressing the oil. Hempseed oil generally also contains omega-6 and omega-3 fatty acids. For example, about 30-35% of the weight of hempseed oil are essential fatty acids (EFAs), i.e., linoleic acid, omega-6 (LA, 55%), α-linolenic acid, omega-3 (ALA, 22%), γ-linolenic acid, omega-6 (GLA, 1-4%), and stearidonic acid, omega-3 (SDA, 0-2%). Thus, the compositions of some embodiments may contain fatty acids such as omega-6 and omega-3 fatty acids.

Oils include cannabidiol oil and various plant derived oils containing cannabidiol, such as hemp seed oil, *Echinacea purpurea, Echinacea angustifolia, Acmella oleracea, Helichrysum umbraculigerum, Radula marginata*, and the like. In some embodiments, cannabidiol isolated from such plants or made synthetically may be formulated with an oil such as, for example, olive oil, grapeseed oil, tea tree oil, almond oil, avocado oil, sesame oil, evening primrose oil, sunflower oil, kukui nut oil, jojoba oil, walnut oil, peanut oil, pecan oil, macadamia nut oil, coconut oil, and the like and combinations thereof.

In some embodiments, the compositions may further include a brassinosteroid or combinations of brassinosteroids. Brassinosteroids are a group of compounds related to brassinolide, a C28 steroid with a lactone B-ring structure. Brassinosteroids include, but are not limited to, 24(S) ethylbrassinone analogs, (22R,23R,24S)-2alpha, 3alpha,5alpha,22,23-pentahydroxy-stigmastan-6-one, (22R,23R,24S)-3beta-bromo-5alpha,22,23-trihydroxystigmastan-6-one, (22 S,23 S,24 S)-2alpha,3 alpha,22,23-tetrahydroxy-5alpha, stigmastan-6-one, (22R,23R,24 S)-3beta-acetoxy-22,23-dihydroxy-5alpha-cholestan-6-one, (22S,23 S,24S)-3beta-bromo-22,23-dihydroxy-5alpha-cholestan-6-one, (22S,23 S,24S)-3beta-bromo-5alpha,22,23-trihydroxy-stigmastan-6-one, and (22S,23 S)-3β-bromo-5α,22,23-trihydroxystigmastan-6-one.

The amount of brassinosteroid in the topical formulation is not limited, so long as it is a therapeutically effective amount. In some embodiments, the brassinosteroid may have a concentration of about 0.01 wt. % to about 5 wt. %, relative to the total amount of the composition, about 0.1 wt. % to about 1 wt %, relative to the total amount of the composition, or any range or individual value encompassed by these example ranges.

Without wishing to be bound by theory, the combination of cannabinoid and brassinosteroid may provide enhanced antimicrobial activity compared to the antimicrobial effect of these compounds individually, to the extent either cannabinoids or brassinosteroids exhibit antimicrobial activity. Thus, the compositions of the invention are capable of eliminating the fungi and bacterial, attenuating fungal spores, reducing toxin production, and improving symptoms related to the microbial infection more quickly than either component alone.

In some embodiments, the compositions may further include an anti-inflammatory compound such as hyaluronic acid, curcumin, glutathione, methotrexate, tofacitinib, 6-mercaptopurine, azathioprine sulfasalazine, mesalazine, olsalazine chloroquine/hydroxychloroquine, penicillamine, aurothiomalate (intramuscular and oral), azathioprine, colchicine, corticosteroids (oral, inhaled, and local injection), a beta-2 adrenoreceptor agonist (salbutamol, terbutaline, salmeterol), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adenosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCV acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCIO-469, VX-702, AMG-548, VX-740, Roflumilast, IC-485, CDC-801, S1PI agonists (such as FTY720), a PKC family inhibitor (e.g. Ruboxistaurin or AEB-071) or Mesopram, budesonide; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), an antiinflammatory cytokine (e.g. IL-4, IL-10, IL-11, IL-13 or TGF), therapeutic agents that target an intrinsic checkpoint blockade, such as, for example, the gene encoding Cytokine-inducible $SH_2$-containing protein (CISH), antibody BGB-A317, Nivolumab, or Pembrolizumab, atezolizumab, avelumab, durvalumab, ipilimumab, and the like and combinations thereof.

The amount of anti-inflammatory agent is not limited and includes any therapeutically effective amount. For example, in some embodiments, the amount of anti-inflammatory agent may be about 0.01 wt. % to about 5 wt %, relative to the total amount of the composition, about 0.1 wt. % to about 1 wt %, relative to the total amount of the formulation, or any range or individual concentration encompassed by these example ranges.

In some embodiments, the compositions may further include an antibiotic. The type of antibiotic is not limited, and can be, for example, subtilosin, ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, cefmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam.

The amount of the antibiotic in the compositions is not limited, and includes any therapeutically effective amount. For example, the antibiotic may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments of the present invention, compositions may further contain a mineral, mineral salt, or combinations thereof. Such minerals are not limited, and can include selenium, sulfur, zinc, iron, chlorine, cobalt, copper, manganese, molybdenum, and iodine.

The amount of the mineral or mineral salts in the topical formulation is not limited, and includes any therapeutically effective amount. For example, the mineral or mineral salt may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments of the present invention, the compositions may further include a vitamin or a combination of vitamins. Vitamins are organic molecules that are essential nutrients that organisms need to sustain proper biological function and metabolism. The vitamins encompassed by the invention are not limited, and can be, for example, vitamin A, vitamin $B_1$, vitamin $B_2$, vitamin $B_3$, vitamin $B_4$, vitamin $B_5$, vitamin $B_6$, vitamin $B_7$, vitamin $B_8$, vitamin $B_9$, vitamin $B_{10}$, vitamin $B_{11}$, vitamin $B_{12}$, vitamin C, vitamin D, vitamin E, and vitamin K.

The amount of the vitamin in the topical formulation is not limited, and can be any therapeutically effective amount. For example, the vitamin may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments, the compositions may further contain amino acids, peptides, or combinations thereof. Amino acids are organic compounds that combine through peptide bond formation to form peptides and proteins. Amino acids can chemically combine through peptide bond formation to form dipeptides, tripeptides, tetrapeptides, oligopeptides, polypeptides, peptides, and proteins. Amino acids are the building blocks for living organisms. The human body uses amino acids to break down food, grow, repair body tissue, and perform other necessary biological processes. The amino acid is not limited, and can be at least one member selected from the group consisting of L-arginine, D-arginine, L-histidine, D-histidine, L-lysine, D-lysine, L-aspartic acid, D-aspartic acid, L-glutamic acid, D-glutamic acid, D-serine, L-serine, D-threonine, L-threonine, D-asparagine, L-asparagine, L-glutamine, D-glutamine, L-cystine, D-cysteine, L-selenocysteine, D-selenocysteine, L-glycine, D-glycine, L-proline, D-proline, L-alanine, D-alanine, L-valine, D-valine, L-isoleucine, D-isoleucine, L-leucine, D-leucine, L-methionine, D-methionine, L-phenylalanine, D-phenylalanine, L-tyrosine, D-tyrosine, L-tryptophan, D-tryptophan.

The amount of amino acids, peptides, or combinations thereof in the composition is not limited, and includes any therapeutically effective amount. For example, the amino acid, peptides, or combinations thereof may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments, the compositions may include one or more antioxidants such as, for example, ascorbic acid, ascorbic acid derivatives, glucosamine ascorbate, arginine ascorbate, lysine ascorbate, glutathione ascorbate, nicotinamide ascorbate, niacin ascorbate, allantoin ascorbate, creatine ascorbate, creatinine ascorbate, chondroitin ascorbate, chitosan ascorbate, DNA ascorbate, carnosine ascorbate, vitamin E, vitamin E derivatives, tocotrienol, rutin, quercetin, hesperidin (*Citrus sinensis*), diosmin (*Citrus sinensis*), mangiferin (*Mangifera indica*), mangostin (*Garcinia mangostana*), cyanidin (*Vaccinium myrtillus*), astaxanthin (*Haematococcus algae*), lutein (*Tagetes patula*), lycopene (*Lycopersicum esculentum*), resveratrol (*Polygonum cuspidatum*), tetrahydrocurcumin (*Curcuma longa*), rosmarinic acid (*Rosmarinus officinalis*), hypericin (*Hypericum perforatum*), ellagic acid (*Punica granatum*), chlorogenic acid (*Vaccinium vulgaris*), oleuropein (*Olea europaea*), α-lipoic acid, niacinamide lipoate, glutathione, andrographolide (*Andrographis paniculata*), carnosine, niacinamide, potentilla erecta extract, polyphenols, grape seed extract, pycnogenol (pine bark extract), pyridoxine, magnolol, honokiol, paeonol, resacetophenone, quinacetophenone, arbutin, kojic acid, and the like and combinations thereof.

In some embodiments, the compositions may include one or more essential oil. Essential oils refer to synthetic or natural oils derived from any source, but particularly from the flowers, seeds, fruits, roots, bark, sap, herbs, trees, and other plants. Such essential oils can generally be extracted by methods known in the art. Essential oils are generally aromatic and are typically named for the plant from which the oil is extracted. For example, rose oil or peppermint oil are derived from rose or peppermint plants, respectively. Examples of essential oils that can be used in the compositions of the invention include, but are not limited to, sesame oil, macadamia nut oil, tea tree oil, evening primrose oil, sage oil, coriander oil, thyme oil, pimento berries oil, rose oil, almond oil, anise oil, balsam oil, bergamot oil, rosewood oil, camphor oil, cardamom oil, cedar oil, cedar leaf oil, chamomile oil, cinnamon oil, sage oil, clary sage oil, clove oil, clove leaf oil, cypress oil, eucalyptus oil, fennel oil, fistree oil, sea fennel oil, frankincense oil, geranium oil, ginger oil, grapefruit oil, jasmine oil, jojoba oil, juniper oil, lavender oil, lemon oil, lemongrass oil, lime oil, mandarin oil, marjoram oil, myrrh oil, menthol, neroli oil, orange oil, patchouli oil, pepper oil, black pepper oil, petitgrain oil, pine seed oil, pine needle oil, rosehip oil, rose otto oil, rosemary oil, sandalwood oil, spearmint oil, spikenard oil, vetiver oil, walnut oil, whitepine oil, wintergreen oil, ylang ylang, and the like and combinations thereof. The amount of essential oil in such embodiments may be about 0.01 wt. % to about 10 wt. %, about 0.1 wt. % to about 5 wt. % based on the total weight of the composition, or any individual concentration or range encompassed by these ranges.

In some embodiments, the compositions may include one or more exfoliating agents. The exfoliating agents can be a chemical exfoliant or exfoliating particles of, for example, minerals, vegetables, organic particles, water-swellable pulverulent polymers (powder or beads), polyethylene particles (beads or powders), jojoba spheres, ground shells of fruit stones, pumice stone, glass beads, aluminium oxide, and the like and combinations or mixtures thereof. Exfoliating agents are present in variable amounts depending on the intended result. For example, the concentration of exfoliating agents may be about 2 wt. % to about 80 wt. % of the composition.

Creams refer to semi-solid emulsions of oil and water in approximately equal proportions. They are divided into two types: oil-in-water (O/W) creams, composed of small droplets of oil dispersed in a continuous phase; and water-in-oil (W/O) creams, composed of small droplets of water dispersed in a continuous oily phase. Creams can provide a barrier to protect the skin. This may be a physical barrier or a chemical barrier as with UV-absorbing compounds. To aid in the retention of moisture (especially water-in-oil creams), creams are usually used for a variety of purposes including cleansing, emollient effects, and as a vehicle for drug substances such as local anesthetics, anti-inflammatories (NSAIDs or corticosteroids), hormones, antibiotics, antifungals or counter-irritants.

Liniments or balms are topical formulations that are of a similar viscosity to lotions and less viscous than an ointment or cream. Liniments are generally applied with friction by rubbing the liniment into the skin. Liniments typically are formulated from alcohol, acetone, or similar quickly evaporating solvents and may contain counterirritant aromatic chemical compounds such as methyl salicylate, benzoin resin, or capsaicin.

Ointments are compositions in which oil and water are provided in a ratio of from 7:1 to 2:1, from 5:1 to 3:1, or 4:1. Ointments are generally formulated using oils, waxes, water, alcohols, petroleum products, water, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value.

Lotions are low- to medium-viscosity topical preparation. Most lotions are oil-in-water emulsions containing an emulsifier such as cetyl alcohol to prevent separation of these two phases. Lotions can include fragrances, glycerol, petroleum jelly, dyes, preservatives, proteins and stabilizing agents.

In some embodiments, the formulations can be in the form of a soap, which are formulations that comprise a salt of a fatty acid. Soaps are mainly used as surfactants for washing, bathing, and cleaning, but they are also used in textile spinning and are important components of lubricants. Soaps for cleansing can be obtained by treating vegetable or animal oils and fats with a strongly alkaline solution. Fats and oils are composed of triglycerides; three molecules of fatty acids are attached to a single molecule of glycerol. The alkaline solution, which is often called lye (although the term "lye soap" refers almost exclusively to soaps made with sodium hydroxide), is believed to promote a chemical reaction known as saponification. In saponification, fats are first hydrolyzed into free fatty acids, which then combine with the alkali to form crude soap. Glycerol (glycerine) is usually liberated and is either left in or washed out and recovered as a useful byproduct, depending on the process employed.

In some embodiments, the composition can be in the form of a shampoo, which is a hair care product used for the removal of oils, dirt, skin particles, dandruff, environmental pollutants and other contaminant particles that gradually build up in hair. A goal may be to remove the unwanted build-up without stripping out so much sebum asto make hair unmanageable.

In some embodiments, the composition can be in the form of a tincture. Tinctures are herbal extracts that provide a method for oral administration of an herbal component or components to a subject in need of treatment. Tinctures are prepared by mixing an herb or herbs or components and combinations thereof with a suitable solvent wherein a component or components of an herb or herbs or combinations thereof are extracted into a solvent in which the component or components of the herb are reasonably soluble. Suitable tincture solvents in the present invention include pharmacologically acceptable solvents such as organic solvents, water based solvents, alcohols, and other orally administrable solvents such as, but not limited to, water, purified water, preserved water, vegetable glycerin, propylene carbonate, 3-methoxy-3-methyl-1-butanol (MMB), polyethylene glycol, glycerol, rice bran oil, and combinations thereof.

In some embodiments, the composition can be in the form of a tonic. Tonics are extracts that provide a method for oral administration of an herbal component or components to a subject in need of treatment. Tonics are prepared by mixing an herb or herbs or components and combinations thereof with a suitable solvent wherein a component or components of an herb or herbs or combinations thereof are extracted into a solvent by aid of heating, often heat necessary such that the solvent reaches its boiling temperature, in which the component or components of the herb are reasonably soluble. Suitable tonic solvents in the present invention include pharmacologically acceptable solvents such as organic solvents, water based solvents, alcohols, and other orally administrable solvents such as, but not limited to, water, purified water, preserved water, vegetable glycerin, propylene carbonate, 3-methoxy-3-methyl-1-butanol (MMB), polyethylene glycol, glycerol, rice bran oil, and combinations thereof.

In certain embodiments, antimicrobial compositions may be a tincture containing about 10 wt. % to about 40 wt. % cannabidiol or cannabigerol and about 0.01 wt. % to about 5 wt. % brassinosteroid or combination of brassinosteroid. Such compositions may be used for various particular types of microbial infections. Specific formulations may be used to treat specific microbial infections.

For example, some embodiments include a nail bed balm. Such nail bed balms may include about 10 wt. % to about 40 wt. % cannabinoid, about 0.01 wt. % to about 5 wt. % brassinosteroid or combination of brassinosteroid, about 0.01 wt. % to about 5 wt. % of one or more essential oils, and about 0.5 wt. % to about 5 wt. % penetration enhancer. In particular embodiments, the one or more essential oils may be about 0.01 wt. % to about 5 wt. % tea tree oil and about 0.01 wt. % to about 5 wt. % primrose oil, and the penetration enhancer may be hyaluronic acid. In some embodiments, the cannabinoid may be cannabidiol (CBD) or cannabigerol (CBG), and in certain embodiments, the cannabinoid may be CBG. The composition may be a liquid or solid composition dissolved or diluted in a carrier suitable for application to the skin such as, for example, biocompatible oil bases, wax bases, lotion bases, balm bases, salve bases, ointment bases, and the like. The various components of these carriers are well known to those of ordinary skill in the art. In some embodiments, the compositions may include a balm base that allows for easy application and absorption.

Some embodiments include a foot cream. Such foot creams may include about 10 wt. % to about 40 wt. % cannabinoid and about 0.01 wt. % to about 5 wt. % brassinosteroid or combination of brassinosteroid in a cream or balm base. In certain embodiments, the cream or balm base may include additional components such as fruit juices or oils, sugar, essential oils, moisturizers, penetration enhancers, exfoliating agents, and the like and combinations thereof. In certain embodiments, the fruit juice or fruit oils in such embodiments may be lemon or apple juice or oil, and such juices or oils may be about 5 wt. % to about 20 wt. % of the composition based on the total weight of the composition. In some embodiments, the essential oils may be primrose oil, and the concentration of essential oils may be about 0.01 wt. % to about 5 wt. %. In some embodiments, the penetration enhancer may be hyaluronic acid, and the penetration enhancer may be about 0.5 wt. % to about 5 wt. % of the composition. The type and amount of exfoliating agents may depend on the extent to which exfoliation is desired. For example, in some embodiments, the exfoliating agent may be about 2 wt. % to 30 wt. % or 2 wt. % to about 25 wt. % based on the total weight of the composition. Exfoliating agents may include, for example, polyethylene particles, jojoba spheres, ground shells of fruit stones, pumice stone, glass beads, aluminium oxide.

Other embodiments include acne treatment and acne treatment kits that include a tincture containing about 10 wt. % to about 40 wt. % cannabinoid and about 0.01 wt. % to about 5 wt. % brassinosteroid or combination of brassinosteroid in a tincture solutions such as organic solvents, water based solvents, alcohols, vegetable glycerin, propylene carbonate, 3-methoxy-3-methyl-1-butanol (MMB), polyethylene glycol, glycerol, rice bran oil, and the like and combinations thereof. In some embodiments, such compositions may further include anti-acne agents such as, for example, retinoids such as tretinoin, isotretinoin, motretinide, adapalene, tazarotene, azelaic acid, and retinol, salicylic acid, benzoyl peroxide, resorcinol, sulfur, sulfacetamide, urea, essential oils, alpha-bisabolol, dipotassium glycyrrhizinate, camphor, β-glucan, allantoin, feverfew, flavonoids such as soy isoflavones, saw palmetto, chelating agents such as EDTA, hydrolyzed vegetable proteins, inorganic ions of chloride, iodide, fluoride, and their nonionic derivatives chlorine, iodine, fluorine, phospholipids, and combinations thereof. In such embodiments, the anti-acne agent may be about 0.1 wt. % to about 10 wt. %, about 1 wt. % to about 5 wt. %, or any individual concentration or range encompassed by these ranges.

In some embodiments, the composition may be a moisturizer containing about 10 wt. % to about 40 wt. % cannabinoid and about 0.01 wt. % to about 5 wt. % brassinosteroid or combination of brassinosteroid, about 0.1 wt. % to about 10 wt. % anti-acne agent, 5 wt. % or more essential oils, for example, about 0.01 wt. % to about 5 wt. % tea tree oil and about 0.01 wt. % to about 5 wt. % primrose oil, about 0.01 wt. % to about 2 wt. % antioxidant, about 0.01 wt. % to about 2 wt. % vitamins, and in some embodiments, about 0.5 wt. % to about 5 wt. % penetration enhancer. In some embodiments, the antioxidant and vitamin may be glutathione, Vitamin C, ascorbate, or combinations thereof, and the penetration enhancer may be hyaluronic acid.

Some embodiments include facial cleansers that contain about 10 wt. % to about 40 wt. % cannabinoid and about 0.01 wt. % to about 5 wt. % brassinosteroid or combination of brassinosteroid, 5 wt. % or more essential oils, for example, about 0.01 wt. % to about 5 wt. % tea tree oil and about 0.01 wt. % to about 5 wt. % primrose oil, and about 0.01 wt. % to about 2 wt. % antioxidant, about 0.01 wt. % to about 2 wt. % vitamins. In some embodiments, the antioxidant and vitamin may be glutathione, Vitamin C, ascorbate, or combinations thereof.

In some embodiments, the composition may be a universal cleanser containing about 10 wt. % to about 40 wt. % cannabinoid and about 0.01 wt. % to about 5 wt. % brassinosteroid or combination of brassinosteroid, 5 wt. % or more essential oils, for example, about 5 wt. % or more primrose oil, and about 0.5 wt. % to about 5 wt. % penetration enhancer. In some embodiments, the penetration enhancer may be hyaluronic acid.

In some embodiments, the facial cleanser or universal cleanser may be disposed on a fibrous material to create wipes. In such embodiments, the fibrous material may include a single layer of a substantially homogeneous material, for example, an air laid web of fibers that are uniformly mixed or distributed throughout the web. The fibrous material may be composed of polymeric fibers such as polyester, polyethylene, and polypropylene, natural or synthetic fibers such as cellulosic fibers, and the like and combinations thereof. In some embodiments, the fibrous material may be composed of a co-formed web of polypropylene and cellulosic fibers with fibers uniformly mixed throughout the web. In some embodiments, the fibrous material may include a nonwoven, layered basesheet. The layered base sheet may include at least two layers in which one of the layers includes fibers that are not included in the other layer, for example, at least one of the layers may include polyethylene fibers and at least one of the layers may include polypropylene fibers. In some embodiments, the layers may include similar or the same materials, but in differing amounts. The different layers can be configured to provide different physical properties, for example, one layer may provide softness, while another layer provides strength to the wipe product.

Wipes may be packaged as a stack of sheets moistened with the facial cleanser composition or universal cleanser composition. Such wet wipes may be used for baby wipes, hand wipes, household cleaning wipes, industrial wipes, body wipes, and facial wipes, and the like and combinations thereof.

Further embodiments include a sunscreen containing about 10 wt. % to about 40 wt. % cannabinoid and about 0.01 wt. % to about 5 wt. % brassinosteroid or combination of brassinosteroid, 5 wt. % or more essential oils, for example, about 0.01 wt. % to about 5 wt. % tea tree oil and about 0.01 wt. % to about 5 wt. % primrose oil, and about 5 wt. % to about 15 wt. % zinc oxide.

Tables 1-3 below provide specific examples of formulations encompassed by the invention. The compositions of Table 1 include Retinol and/or hyaluronic acid, which are optional ingredients, but that may be beneficial in certain applications.

TABLE 1

| | |
|---|---|
| CBD or analog or combinations thereof | 1.0-30% (w/w) |
| Brassinosteroid or analog or combinations thereof | 30-100 µM |
| Subtilosin | 40-100 mg/mL |
| Retinol | 0.5% (w/w) |
| Hyaluronic acid | 0.5-1.5% (w/w) |
| Glutathione | 800-1500 mg |
| Vitamin C | 350-1000 mg |
| L-lysine | 1000-3000 mg |
| Selenium | 55-125 mg |
| Sulfur | 1000-1500 mg |
| Zinc | 10-15 mg |

The compositions of Table 2 do not include Retinol or hyaluronic acid, but are effective for treating bacterial infections.

TABLE 2

| | |
|---|---|
| CBD or analog or combinations thereof | 1.0-30% (w/w) |
| Brassinosteroid or analog or combinations thereof | 30-100 µM |
| Subtilosin | 40-100 mg/mL |
| Glutathione | 800-1500 mg |
| Vitamin C | 350-1000 mg |
| L-lysine | 1000-3000 mg |
| Selenium | 55-125 mg |
| Sulfur | 1000-1500 mg |
| Zinc | 10-15 mg |

The compositions of Table 3 quercetin, but do not include Retinol
or
hyaluronic acid. Such compositions are effective at treating bacterial infections and are beneficial in certain applications.

TABLE 3

| | |
|---|---|
| CBD or analog or combinations thereof | 1.0-30% (w/w) |
| Brassinosteroid or analog or combinations thereof | 30-100 µM |
| Quercetin | 1.5-150 mg/mL |
| Glutathione | 800-1500 mg |
| Vitamin C | 350-1000 mg |
| L-lysine | 1000-3000 mg |
| Selenium | 55-125 mg |
| Sulfur | 1000-1500 mg |
| Zinc | 10-15 mg |

Various embodiments are directed methods for preventing, inhibiting proliferation of, or treating microbial infections by administering any of the compositions described above including cannabinoids, and in some embodiments, brassinosteroids to the subject in need of treatment. Administering can be carried out topically. The fungi treated and symptoms associated with these microbial infections include any of those described above. Antimicrobial formulations may produce a reduction in dermatological microbial infection symptoms, while improving the condition of the affected skin zones following treatment. The compositions of various embodiments can be used to aid healing of microbial infection induced tissue wounds.

Another embodiment of the present invention is a method of making the topical formulation in the form of a cream, which comprises (i) dispersing lake/powder into mineral oil or silicone oil to obtain an oil phase; (ii) dispersing an emulsifier, a thickener; and a stabilizer into water in a separate vessel to obtain an aqueous phase; (iii) blending the oil phase and the aqueous phase to form an emulsion; and (iv) dispersing an active ingredient such as a *Cannabis* derived botanical drug product into at least one of the oil phase, the aqueous phase, and the emulsion. In some embodiments, the method further comprises heating during at least one of (i) dispersing lake/powder into mineral oil or silicone oil to obtain an oil phase and (ii) dispersing an emulsifier, a thickener; and a stabilizer into water in a separate vessel to obtain an aqueous phase. Temperatures of this heating are not particularly limited, so long as the oil phase and the aqueous phase result from the dispersing.

Another embodiment of the present invention is a method of making the topical formulation in the form of a lotion, which comprises mixing an oil phase comprising hemp oil with an emulsifier and with an aqueous phase to form a mixture and heating said mixture at a temperature of from 45 and 85° C. to form an aqueous emulsion. Emulsifiers include, but are not limited to, cetyl alcohol, stearic acid, and a mixture thereof. The water phase comprises a stabilizing agent such as VEEGUM® or CARBOPOL®.

Another embodiment of the present invention is a method of making the topical formulation in the form of a shampoo, which comprises combining a surfactant, most often sodium lauryl sulfate and/or sodium laureth sulfate with a co-surfactant, most often cocamidopropyl betaine, in an aqueous phase and mixing the aqueous phase to form a thick, viscous liquid. Preferred methods further comprise adding other ingredients, such as salt (sodium chloride), a preservative, and fragrance, to the aqueous phase.

Another embodiment of the present invention is a method of treating manifestations of dermatological conditions caused by a microbial infection, which comprises applying a therapeutically effective amount of the topical formulation, according to the present invention, to skin affected with a dermatological condition. Non-limiting examples of targeted dermatological conditions include blisters, sores, discoloration, and the like.

Unless indicated otherwise, the term "therapeutically effective amount" is not particularly limited, so long as at least one of THC and CBD is present in an amount effective for treating the dermatological disease. Preferably, the therapeutically effective amount of at least one of THC and CBD is from 2 to 100 milligrams per kilogram, more preferably from 2 to 50 milligrams per kilogram, and more preferably from 2 to 25 milligrams per kilogram. The most preferred therapeutically effective amount of THC and/or CBD in the topical formulation according to the present invention is from 2 to 10 milligrams per kilogram. All rational numbers between the preceding minima and maxima are included in the ranges.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

The following formulation was prepared as a balm:

TABLE 4

| | |
|---|---|
| Brassinosteroids | 383 uL of 0.001 mg/mL solution |
| Glutathione | 0.67 g |
| Lysine | 2 g |
| Ascorbyl Palmitate | 0.5 g |
| Zinc Citrate | 571 uL of 0.001 mg/mL solution |
| Cannabidiol | 0.5 g |
| Selenomethionine | 2 mg |
| Hyaluronic acid | 0.2 g |
| Distilled water | 3 mL |
| Polysorbate-20 | 3 mL |
| Polysorbate-80 | 0.8 mL |

The formulation above may further include 20 g of one or more of grapeseed oil, yellow beeswax, peppermint oil, organic coconut oil, sweet basil leaf oil, black pepper oil, roman chamomile flower oil, german chamomile flower oil, cinnamon leaf oil, citronella oil, eucalyptus leaf oil, helichrysum flower oil, ginger root oil, pink grapefruit peel oil, juniper berry oil, lemongrass oil, pine needle oil, ravensara oil, rosemary leaf oil, spearmint oil, wild oregano oil, organic cypress oil, fennel oil, lemon peel oil, lavender flower oil, and the like, which can be used to modify the consistency of the formulation and add flavor.

The various ingredients were weighed and combined. The zinc citrate solution was added to these dry ingredients. Distilled water, Polysorbate-20, and Polysorbate-80 were then added to this mixture. The solution was heated until liquid, approximately 80° C. The solution was added to containers at 80° C. and allowed to cool to room temperature When essential oil is added to the formulation, the oil is added to the ingredient mixture and stirred at approximately 80° C. until the liquid has a uniform consistency. This solution is added to containers at 80° C. and allowed to cool to room temperature.

Figure 1B:
FIG. 1B is a photograph showing the patient in FIG. 1A 12 hours after treatment.
Figure 1C:
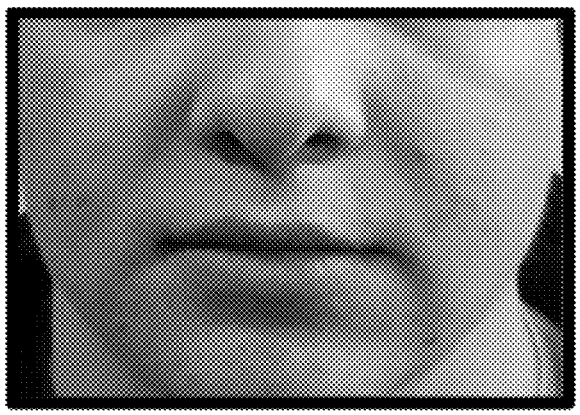
FIG. 1C is a photograph showing the patient in FIG. 1A 24 hours after treatment.
Figure 1D:
FIG. 1D is a photograph showing the patient in FIG. 1A 72 hours after treatment.

FIG. 1A shows an outbreak of papules and pustules on the patient's face caused by Acne. The cream formulation from Table 4 was applied once daily to the skin in an amount sufficient to cover the infected area and surrounding uninfected skin. Twelve hours after application (FIG. 1B), the amount of papules and pustules was markedly reduced indicating a reduction of bacterial presence. Some redness associated with immune response is still present. Symptoms of infection were absent after 24 hours of application twice daily (FIG. 1C), and redness associated with immune response is limited to areas immediately adjacent to the individual papules and pustules. After 72 hours (FIG. 1D), redness associated with immune response is very limited indicating that the infection is eliminated and the skin is healing, and no new breakouts of acne have occurred.

Example 2

A cream was created containing the ingredients in TABLE 5 in a cream base:

TABLE 5

| | |
|---|---|
| CBD | 0.9% |
| CBG | 0.1% |
| Hyaluronic acid | 0.9% |
| Nicotinamide | 5.0% |

Base components (non-active ingredients): Organic Aloe Leaf Juice, Organic Sweet Almond Oil, Organic Alcohol Extract of Blueberry Fruit, Glyceryl Stearate, Stearic Acid, Organic Glycerin, ProVitamin B5, Vitamin E, Organic Avocado Fruit Oil Infusion of Calendula Flower, Chamomile Flower, Lavender Flower and Red Clover Flower, Organic Olive Oil, Organic Sunflower Seed Oil, Organic Evening Primrose Oil, Meadowfoam Seed Oil, Organic Jojoba Seed Oil, Organic Shea Butter, Organic Cocoa Butter, Organic Macadamia Nut Oil, Vitamin A Ester, Lime Peel Essential Oil, Atlas Cedarwood Essential Oil, Organic Lavender Flower Essential Oil, Tangerine Peel Essential Oil, Organic Neem Seed Oil, Organic Rosemary Leaf Extract, and Xanthan Gum.

Figure 2A:
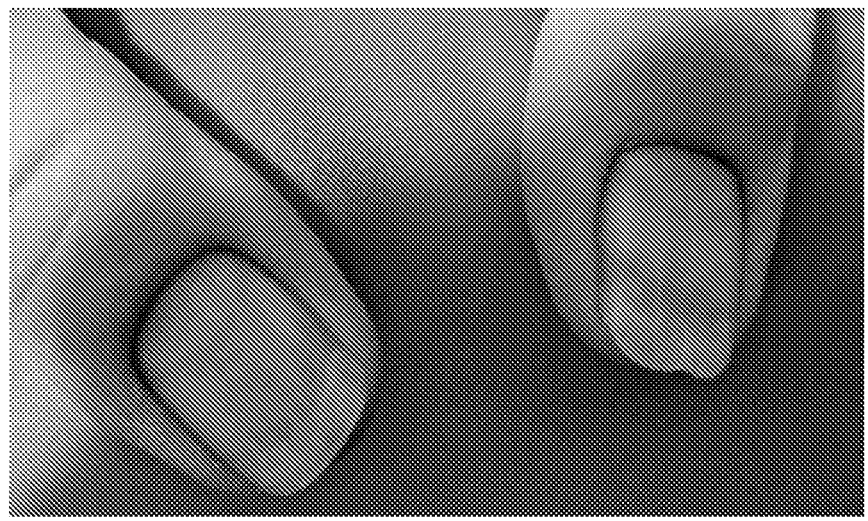
FIG. 2A is a photograph of the fingers of a patient exhibiting symptoms of the fungal infection surrounding her nails.
Figure 2B:
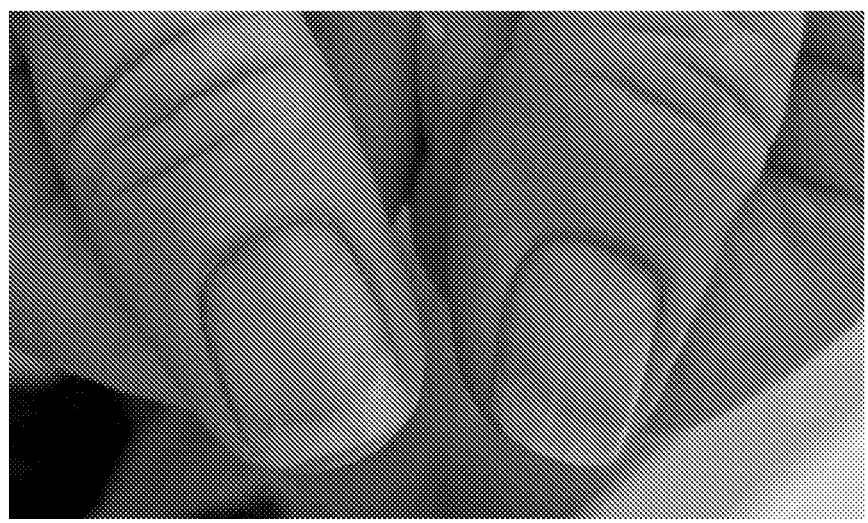
FIG. 2B is a photograph of the same fingers of the patient in FIG. 1 two weeks following treatment with the compositions of the invention.

The above cream was applied topically to the nails of a patient having fungal growth extending around the nail bed that produced darkening of the skin surrounding the nail (FIG. 2A). Shortly after administration inflammation and redness associated with the fungal infection was noticeably reduced. After 2 weeks of topical administration of the cream once per day, inflammation and redness was eliminated, darkening of the skin surrounding the nails was eliminated, and other signs of infection were significantly reduced (FIG. 2B). In addition, the overall health of the nail improved as indicated by smoother appearance and reduction in brittleness.

Example 3

A cream composition was created containing the ingredients in TABLE 6 in a cream base:

TABLE 6

| | |
|---|---|
| CBG | 1.0% |
| Tea Tree Oil | 5.0% |
| Hyaluronic acid | 1.0% |

Base components (non-active ingredients): Organic Aloe Leaf Juice, Organic Sweet Almond Oil, Organic Alcohol Extract of Blueberry Fruit, Glyceryl Stearate, Stearic Acid, Organic Glycerin, ProVitamin B5, Vitamin E, Organic Avocado Fruit Oil Infusion of Calendula Flower, Chamomile Flower, Lavender Flower and Red Clover Flower, Organic Olive Oil, Organic Sunflower Seed Oil, Organic Evening Primrose Oil, Meadowfoam Seed Oil, Organic Jojoba Seed Oil, Organic Shea Butter, Organic Cocoa Butter, Organic Macadamia Nut Oil, Vitamin A Ester, Lime Peel Essential Oil, Atlas Cedarwood Essential Oil, Organic Lavender Flower Essential Oil, Tangerine Peel Essential Oil, Organic Neem Seed Oil, Organic Rosemary Leaf Extract, and Xanthan Gum.

Figure 3A:
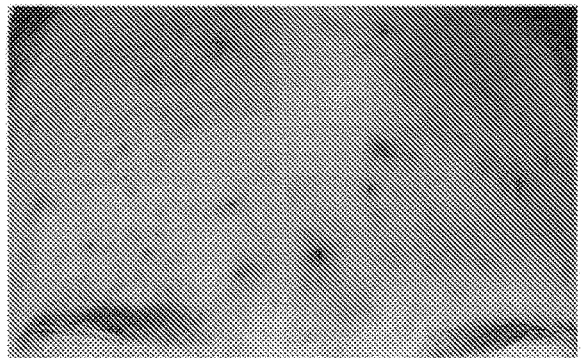
FIG. 3A is a photograph showing a patient exhibiting symptoms of the acne before treatment with the compositions of the invention.
Figure 3B:
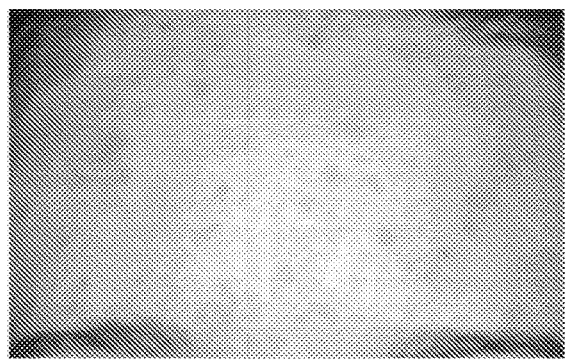
FIG. 3B is a photograph showing the patient in FIG. 3A 7 days after the initial treatment.
Figure 3C:
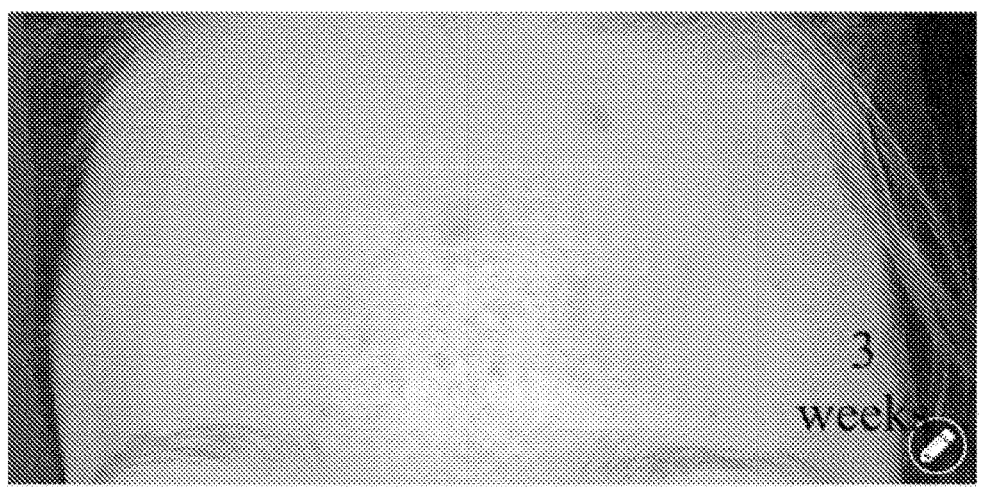
FIG. 3C is a photograph showing the patient in FIG. 3A 3 weeks after the initial treatment.

FIG. 3A shows an outbreak of papules and pustules on the patient's face caused by acne. The cream formulation from Table 6 was applied once daily to the skin in an amount sufficient to cover the infected area and surrounding uninfected skin. Seven days after the initial application with daily reapplication to the same area (FIG. 3B), the amount of papules and pustules was markedly reduced indicating a reduction of bacterial presence. Symptoms of infection were absent after 3 weeks of daily application (FIG. 3C), and redness associated with immune response is limited to areas immediately adjacent to the individual papules and pustules.

Example 4

Additional examples of compositions include the following:

Tincture

The following formulation was prepared as 30 mL of an oral tincture.

TABLE 7

| | |
|---|---|
| Brassinosteroids | 576 uL of 0.001 mg/mL solution |
| Glutathione | 1 g |
| Lysine | 1 g |
| Ascorbyl Palmitate | 0.5 g |
| Zinc Citrate | 861 uL of 0.001 mg/mL solution |
| Cannabidiol | 0.5 g |
| Selenomethionine | 3 mg |
| BioQ | 40 mg |
| Distilled water | 10 mL |
| Polysorbate-20 | 3 mL |
| Polysorbate-80 | 0.8 mL |

The glutathione, lysine, zinc citrate, brassinosteroids, selenomethionine, and BioQ were dissolved into water. The ascorbyl palmitate and cannabidiol were dissolved into 14 mL sweet almond oil. The aqueous and organic solutions were combined to create a biphasic mixture. The polysorbate was added and the resulting mixture was stirred until a uniform opaque yellow mixture at room temperature.

Preventive Balm

The following formulation was prepared as 30 mL of a preventive balm.

TABLE 8

| | |
|---|---|
| Glutathione | 0.67 g |
| Lysine | 0.67 g |
| Ascorbyl Palmitate | 0.5 g |
| Zinc Citrate | 571 uL of 0.001 mg/mL solution |
| Cannabidiol | 0.5 g |
| Selenomethionine | 2 mg |
| Hyaluronic acid | 0.2 g |
| Distilled water | 10 mL |
| Polysorbate-20 | 3 mL |
| Polysorbate-80 | 0.8 mL |

The formulation above may further include 20 g of one or more of grapeseed oil, yellow beeswax, peppermint oil, organic coconut oil, sweet basil leaf oil, black pepper oil, roman chamomile flower oil, german chamomile flower oil, cinnamon leaf oil, citronella oil, eucalyptus leaf oil, *Helichrysum* flower oil, ginger root oil, pink grapefruit peel oil, juniper berry oil, lemongrass oil, pine needle oil, ravensara oil, rosemary leaf oil, spearmint oil, wild oregano oil, organic cypress oil, fennel oil, lemon peel oil, lavender flower oil, and the like, which can be used to modify the consistency of the formulation and add flavor.

The various ingredients were weighed and combined. The zinc citrate solution was added to these dry ingredients. Distilled water, Polysorbate-20, and Polysorbate-80 were then added to this mixture. The solution was heated until liquid, approximately 80° C. The solution was added to containers at 80° C. and allowed to cool to room temperature.

When essential oil is added to the formulation, the oil is added to the ingredient mixture and stirred at approximately 80° C. until the liquid has a uniform consistency. This solution is added to containers at 80° C. and allowed to cool to room temperature.

The invention claimed is:
1. An encapsulated composition consisting essentially of a brassinosteroid selected from the group consisting of (22R,23R,24S)-2a,3a,5a,22,23-pentahydroxy-stigmastan-6-one, (22R,23R,24S)-36-bromo-5a,22,23-trihydroxystigmastan-6-one, (228,238,248)-2a,3a,22,23-tetrahydroxy-5a,stigmastan-6-one, (22R,23R,24S)-36-acetoxy-22,23-dihydroxy-Sa-cholestan-6-one, (228,238,248S)-38-bromo-22,23-dihydroxy-5a-cholestan-6-one, (228,238,24S)-3f-bromo-5a,22,23-trihydroxy-stigmastan-6-one, and (22S, 238)-36-bromo-5a,22,23-trihydroxystigmastan-6-one; cannabidiol, hyaluronic acid and evening primrose oil.

* * * * *